United States Patent
Javois (12) 
(10) Patent No.: US 10,143,456 B2
(45) Date of Patent: Dec. 4, 2018

(54) LEFT ATRIAL APPENDAGE OCCLUSION DEVICE

(76) Inventor: Alex Javois, Hinsdale, IL (US)

( * ) Notice: Subject to any disclaimer, the term of this patent is extended or adjusted under 35 U.S.C. 154(b) by 1456 days.

(21) Appl. No.: 11/245,421

(22) Filed: Oct. 7, 2005

(65) Prior Publication Data

US 2007/0083230 A1   Apr. 12, 2007

(51) Int. Cl.
*A61B 17/00* (2006.01)
*A61B 17/12* (2006.01)

(52) U.S. Cl.
CPC .... *A61B 17/0057* (2013.01); *A61B 17/12122* (2013.01); *A61B 17/12172* (2013.01); *A61B 17/12022* (2013.01); *A61B 2017/00575* (2013.01); *A61B 2017/00579* (2013.01); *A61B 2017/00592* (2013.01); *A61B 2017/00597* (2013.01); *A61B 2017/00615* (2013.01); *A61B 2017/00632* (2013.01); *A61B 2017/00867* (2013.01)

(58) Field of Classification Search
USPC ............... 606/213, 191, 200, 151, 157, 158; 623/1.46, 1.12, 1.18, 1.22, 1.23
See application file for complete search history.

(56) References Cited

U.S. PATENT DOCUMENTS

| | | | |
|---|---|---|---|
| 5,649,959 A | | 7/1997 | Wallace et al. |
| 5,853,422 A | * | 12/1998 | Huebsch et al. ............. 606/213 |
| 5,911,734 A | * | 6/1999 | Tsugita et al. ................ 606/200 |
| 6,010,517 A | * | 1/2000 | Baccaro ........................ 606/151 |
| 6,024,765 A | | 2/2000 | Wallace et al. |
| 6,033,423 A | | 3/2000 | Ken et al. |
| 6,059,825 A | | 5/2000 | Hobbs et al. |
| 6,080,182 A | * | 6/2000 | Shaw et al. .................... 606/213 |
| 6,117,157 A | | 9/2000 | Tekulve et al. |
| 6,152,144 A | * | 11/2000 | Lesh et al. ..................... 128/898 |
| 6,171,329 B1 | * | 1/2001 | Shaw et al. .................... 606/213 |
| 6,206,907 B1 | | 3/2001 | Marino et al. |
| 6,338,736 B1 | * | 1/2002 | Boosfeld et al. ............. 606/191 |
| 6,375,671 B1 | | 4/2002 | Kobayashi et al. |
| 6,463,317 B1 | | 10/2002 | Kucharczyk et al. |
| 6,537,293 B1 | * | 3/2003 | Berryman et al. ............ 606/200 |
| 6,569,179 B2 | * | 5/2003 | Teoh et al. .................... 606/191 |

(Continued)

FOREIGN PATENT DOCUMENTS

| | | |
|---|---|---|
| WO | WO 01/030266 A1 | 5/2001 |
| WO | WO 01/045571 A1 | 6/2001 |
| WO | WO 2005/034764 A1 | 4/2005 |

OTHER PUBLICATIONS

Al-Saady et al., "Left atrial appendage: structure, function, and role in thromboembolism," Heart, 82:547-554 (1999).

(Continued)

*Primary Examiner* — Robert Lynch
(74) *Attorney, Agent, or Firm* — Foley & Lardner LLP (57) ABSTRACT

A left atrial appendage occlusion device includes a deformable wire having a proximal portion and a distal portion, wherein the deformable wire is configured to form a first predetermined expanded shape and a second predetermined relaxed shape; a distal anchor that includes a plurality of hooks or barbs extending from a point at an overall distal end of the deformable wire, the distal anchor being configured to attach the device to an interior wall of the left atrial appendage; and a sheet attached to the proximal portion of the deformable wire.

12 Claims, 6 Drawing Sheets

(56) References Cited

U.S. PATENT DOCUMENTS

| | | |
|---|---|---|
| 6,652,555 B1 * | 11/2003 | VanTassel et al. ........... 606/200 |
| 6,723,108 B1 | 4/2004 | Jones et al. |
| 6,790,218 B2 * | 9/2004 | Jayaraman ................... 606/191 |
| 2002/0002382 A1 * | 1/2002 | Wallace et al. ............... 606/191 |
| 2003/0144694 A1 * | 7/2003 | Chanduszko et al. ........ 606/213 |
| 2004/0034366 A1 * | 2/2004 | van der Burg et al. ...... 606/119 |
| 2004/0127935 A1 * | 7/2004 | VanTassel et al. ......... 606/200 |
| 2004/0158282 A1 | 8/2004 | Jones et al. |
| 2004/0186512 A1 | 9/2004 | Bruckheimer et al. |
| 2004/0243168 A1 | 12/2004 | Ferrera et al. |
| 2005/0004598 A1 | 1/2005 | White, Jr. et al. |
| 2005/0038460 A1 | 2/2005 | Jayaraman |

OTHER PUBLICATIONS

Sievert et al., "Precutaneous Left Atrial Appendage Transcatheter Occlusion to Prevent Stroke in Hihg-Risk Patients with Atrial Fibrillation," Circulation, 105:1887-1889 (2002).

Friedman et al., "Percutaneous Epicardial Left Atrial Appendage Closure: Preliminary Results of an Electrogram Guided Approach", Journal of Cardiovascular Electrophysiology, Apr. 2, 2009, pp. 1-8, advanced publication currently only available on the website of the Journal of Cardiovascular Electrophysiology.

* cited by examiner

LEFT ATRIAL APPENDAGE OCCLUSION DEVICE

BACKGROUND OF INVENTION

The left atrial appendage is the small conical projection from the upper anterior portion of the left atrium. Blood pooling in the appendage may arise spontaneously or as a result of atrial fibrillation. When blood pools in the appendage, blood clots can form. The migration of clots from the left atrial appendage to the bloodstream can cause serious problems when they embolize in the arterial system. More than 90% of clots formed during atrial fibrillation are formed in the left atrial appendage. Sievert et al., CIRCULATION 105:1887-1889 (2002). Embolization of these clots is a frequent cause of stroke. Thus, prevention of clot formation in, or clot migration from, the left atrial appendage may reduce the occurrences of stroke in patients with atrial fibrillation.

A common method of reducing the risk of clot formation is treatment with anticoagulants such as warfarin. Such treatment has been an effective method of reducing the incidence of stroke. However, strokes may still occur in patients using anticoagulants if there is a necessary or inadvertent lapse in treatment. Also, many patients who are at risk of stroke are contraindicated from using anticoagulants. Anticoagulant treatment is effective, but the difficulty in treating patients continuously and the high occurrence of contraindication give rise to a need for a different treatment option.

Another method of treatment designed to reduce clotting and embolization leading to stroke is left atrial appendage obliteration. Clearly, obliteration of the appendage will lead to less clotting during atrial fibrillation. Obliteration may occur during open cardiac surgery or via a less invasive thoracoscopic procedure. Many patients with a high risk of stroke are not candidates for such procedures because of their compromised health status. Further, obliteration of the left atrial appendage may have adverse haemodynamic and hormonal effects that have not been fully studied. See Al-Saady et al., HEART 82:547-554 (1999).

The limitations of anticoagulant treatment and surgical obliteration of the left atrial appendage give rise to the need for a less invasive method and device for aiding to prevent migration of clots from the left atrial appendage into the bloodstream.

Various devices have been developed and used for left atrial appendage occlusion. One such device includes a nitinol cage enclosed in an ePTFE membrane. The device is designed to be inserted entirely into the left atrial appendage and has multiple anchors for attachment to the interior wall of the left atrial appendage. Because the device is designed to be inserted entirely in the left atrial appendage, the device must be properly sized to ensure complete occlusion of the left atrial appendage. Improper measurement of the device may lead to increased implantation times or decreased effectiveness of the device if the wrong size is implanted.

Another device includes a wire cage partially covered by an ePTFE membrane. This device is also designed to be inserted entirely within the left atrial appendage and includes no anchors for attachment within the left atrial appendage. As above, improper measurement of this device may result in increased implantation times or decreased effectiveness. Also, the lack of an anchoring mechanism may lead to more serious complications if the device migrates out of the left atrial appendage.

Still another device used for left atrial appendage occlusion includes a double disk nitinol mesh designed to occlude by clamping to the opening of the left atrial appendage. This device does not include anchors for attaching to the musculature of the left atrial appendage and must be sized properly to prevent migration of the device out of the left atrial appendage. Again, improper measurement of the device may lead to increased implantation time or more serious complications.

Thus, the shortcomings of the prior art devices may lead to longer procedures, incomplete occlusion of the left atrial appendage, or serious complications triggered by migration of the device out of the left atrial appendage. Furthermore, conventional devices are oversized, potentially causing stretching of the left atrial appendage. For example, conventional devices may be oversized by 20-25%. Such stretching may lead to erosion or arrhythmia.

SUMMARY OF INVENTION

It is an object of the present invention to provide improved devices and methods for left atrial appendage occlusion that ensure complete occlusion or substantially complete occlusion of the left atrial appendage to aid in the prevention of clot formation and clot migration from the left atrial appendage in order to reduce the risk of stroke in patients with atrial fibrillation.

It is an object of the present invention to provide devices for left atrial appendage occlusion that are effectively anchored to the musculature of the left atrial appendage to prevent excessive movement of the device or migration of the device out of the left atrial appendage.

It is an object of the present invention to provide devices for left atrial appendage occlusion that will provide complete occlusion or substantially complete occlusion of the left atrial appendage independent of the physiology of the patient in order to reduce implantation times and reduce complications caused by an improperly sized device.

One embodiment of the present invention provides a left atrial appendage occlusion device comprising a deformable wire forming a first predetermined expanded shape and a second predetermined relaxed shape; at least one anchor adapted to attach the device to left atrial appendage tissue; and a sheet, wherein the sheet is attached to the wire; wherein the first predetermined expanded shape is substantially linear; wherein the second predetermined relaxed shape is a substantially coiled shape, the substantially coiled shape comprising a plurality of wire orbits; and wherein when the deformable wire forms the second predetermined relaxed shape, the sheet substantially eclipses an interior cross-section of the substantially coiled shape when viewing the substantially coiled shape along the shape's longitudinal axis.

Another embodiment of the present invention provides a left atrial adage occlusion device comprising a deformable wire forming a first predetermined constrained shape and a second predetermined relaxed shape; at least one anchor adapted to attach the device to atrial appendage tissue; and a sheet, wherein the sheet is attached to the wire; wherein the first predetermined constrained shape is substantially linear; wherein the second predetermined relaxed shape is a cone comprising a plurality of wire orbits; and wherein when the deformable wire is substantially unconstrained, the deformable wire forms the second predetermined relaxed shape and the sheet substantially eclipses the interior of the cone when viewing the cone along the cone's longitudinal axis.

Yet another embodiment of the present invention provides a left atrial appendage occlusion device comprising a deformable wire comprising a shape memory alloy, the wire forming a first predetermined expanded shape and a second predetermined relaxed shape and having a proximal end and a distal end; at least one anchor adapted to attach the device to tissue; and fabric attached to the wire; wherein the first predetermined expanded shape is substantially linear and the second predetermined relaxed shape is substantially conical comprising a plurality of loops with diameters generally decreasing from the proximal end of the coil to the distal end of the coil and wherein when the wire is forming the second predetermined relaxed shape, the fabric substantially covers the opening visible when viewing the coil along the coil's longitudinal axis, the opening defined by the loops at the proximal end of the coiled coil.

Still another embodiment of the present invention provides a method of closing a left atrial appendage of a human or animal heart, comprising deploying a wire and sheet assembly into the left atrial appendage of the heart; anchoring the wire member to tissue of the heart; and directing the wire to form a substantially coiled shape so that an opening of the left atrial appendage is substantially covered by the sheet.

It is to be understood that both the foregoing general description and the following detailed description are exemplary and explanatory only, and are not restrictive of the invention as claimed.

BRIEF DESCRIPTION OF THE DRAWINGS

These and other features, aspects, and advantages of the present invention will become apparent from the following description, appended claims, and the accompanying exemplary embodiments shown in the drawings, which are briefly described below

DETAILED DESCRIPTION OF PREFERRED EMBODIMENTS

The present invention provides devices and methods for occluding the left atrial appendage. The device and method may complete occlude the left atrial appendage by preventing any blood flow into the left atrial appendage from occurring, or the device and method may substantially occlude the left atrial appendage by allowing only a minimal amount of blood flow in and out of the left atrial appendage. The device may include an easily deployed wire structure of shape memory material sized to be appropriate for use in any patient. The device may have a sheet of material attached for eclipsing the opening of the left atrial appendage and means for secured attachment substantially within the left atrial appendage. The method may include deploying the device within the left atrial appendage, securely anchoring the device, and ensuring that a sheet of material eclipses the opening of the left atrial appendage. These features are incorporated into the improved devices and methods in order to more effectively prevent blood flow into the left atrial appendage and/or clot formation and clot migration into or out of the left atrial appendage to greatly decrease the risk of stroke in patients with atrial fibrillation.

The following detailed description of the invention illustrates certain exemplary embodiments and allows a better understanding of the claimed invention.

Unless otherwise specified, "a", "an", and "the" as used herein mean "one or more."

Figure 1:
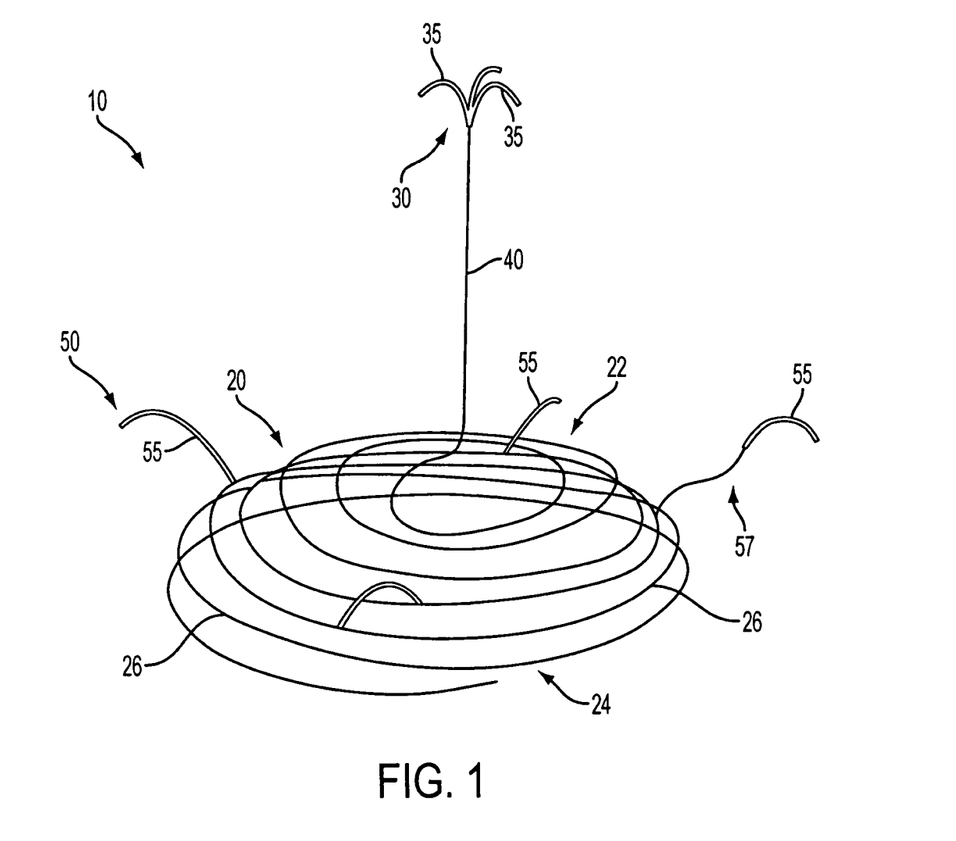
FIG. 1 is a side view of a first embodiment of a left atrial appendage occlusion device.
Figure 2:
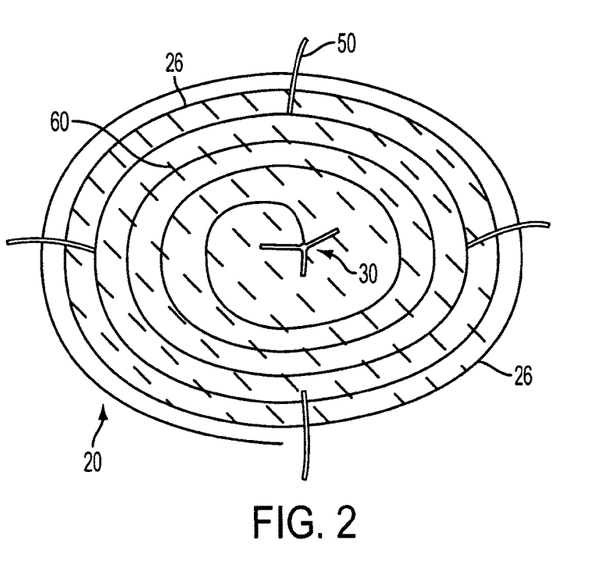
FIG. 2 is a top view of the device of FIG. 1.

FIG. 1 shows a left atrial appendage occlusion device 10 in a relaxed shape. The device has a deformable wire 20 having a proximal end 24 and a distal end 22, wherein the wire 20 is a coil in its relaxed shape having a plurality of orbits connecting the proximal and distal ends. FIG. 1 and FIG. 2 show the wire coil 20 having a conical shape in its relaxed state such that wire orbits at the proximal end 24 define an opening of the coil and have a greater diameter than wire orbits near the distal end 22.

Alternatively, the wire coil 20 may be cylindrically shaped in its relaxed state such that the wire orbits at the proximal end 24 and distal end 22 have substantially the same diameter. Another embodiment includes a wire coil 20 having a conical shape. Other embodiments of the invention may include different relaxed state shapes for the device 10 and wire coil 20 to conform to the physiology of the patient in order to better accomplish the purposes of the device. In an expanded state, the wire 20 is substantially linear. The expanded linear shape allows the device to be delivered to a treatment site via the lumen of a catheter. The relaxed state shape will be shorter than the expanded linear shape along the longitudinal axis of the device. The relaxed state shape will be longer than the expanded linear shape along the axis normal to the longitudinal axis of the device. The relaxed state shape is selected such that wire orbits of the device 10 substantially encompass the interior space of the left atrial appendage to ensure proper placement and functionality of the device.

The wire 20 may be made from any type of suitable shape memory material that will cause the wire to form a preferred relax state configuration when introduced into the left atrial appendage or other treatment site. The material is selected for its biocompatibility including its anti-thrombogenic capacity. The wire 20 material may include Nitinol®, Elgiloy®, titanium, stainless steel, or other suitable material. Shape memory materials are selected for their shape-recovery capabilities and their superelasticity. The material selected may be extended into a substantially linear shape for delivery via a catheter to the left atrial appendage. Upon deployment of the device the material is capable of returning to a predefined relaxed state shape suitable for placement in the left atrial appendage.

The device 10 may have a distal anchoring mechanism 30 at or near its distal end 22. The anchoring mechanism 30 may include one or more distal anchors 35. The distal anchors 35 may be a wire shaped as a hook, barb, or other shape capable of attachment to the musculature of the interior of the left atrial appendage. The distal anchors 35 and distal anchoring mechanism 30 may be made of a different material than the wire 20, such as a stiffer material. The distal anchors 35 and distal anchoring mechanism 30 may be made of sutures. The sutures may be made of any suitable suture material such as nylon, Prolene, or polypropylene. The materials of the distal anchors 35 and distal anchoring mechanism 30 are selected for their biocompatibility and stiffness to ensure proper placement of the device 10 within the left atrial appendage or other treatment site, and to prevent excess movement of the device in order to achieve the purpose of preventing blood flow into the left atrial appendage and/or the migration of clots out of the occluded area.

The distal anchoring mechanism 30 in FIG. 1 includes an attachment wire 40 attached to the wire 20. The attachment wire 40 is attached at its proximal end to the distal end of the wire 20, and the anchor 30 is attached to the distal end of the attachment wire 40. The attachment wire 40 may be more flexible or stiffer than the wire 20. The attachment wire 40 may be a continuation of wire 20, so that the attachment wire 40 and the wire 20 are formed from a single, integral wire. The material for the attachment wire is selected for its stiffness or flexibility to ensure proper placement of the device 10 and minimized clot formation and migration. Thus, the stiffness of the attachment wire may be varied depending on a patient's physiology and movement.

The device 10 of FIG. 1 also includes a proximal anchoring mechanism 50 including one or more proximal anchors 55 attached near the proximal end 24 of the wire 20. Proximal anchoring mechanism 50 may include at least four proximal anchors 55 to ensure proper placement of the device 10. The proximal anchors 55 may be attached to the wire 20 by soldering or other suitable means to insure proper attachment to the wire. The proximal anchors 55 may be a wire shaped as a hook, barb, or other shape capable of attachment to the musculature of the interior of the left atrial appendage to ensure proper placement of the device 10. The proximal anchors 55 may be made of sutures. The sutures may be made of any suitable suture material such as nylon, Prolene, or polypropylene. The materials of the proximal anchors 55 and proximal anchoring mechanism 50 are selected for their biocompatibility and stiffness to ensure proper placement of the device 10 within the left atrial appendage or other treatment site.

The proximal anchoring mechanism 50 may include an attachment wire 57 attached to the wire 20. The attachment wire 57 is attached at its proximal end to a proximal orbit of the wire coil 20, and the anchor 55 is attached to the distal end of the attachment wire 57. The attachment wire 57 may be more flexible or stiffer than the wire 20. The material for the attachment wire is selected for its stiffness or flexibility to ensure proper placement of the device 10 and minimized clot formation and migration.

Figure 6A:
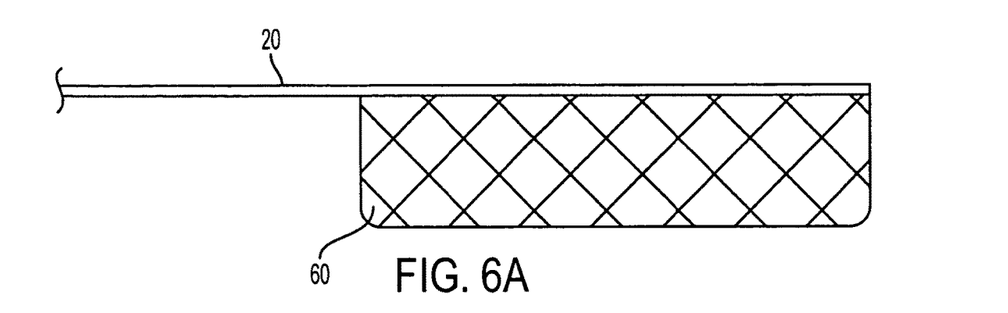
FIG. 6a is a view of a wire in an expanded state with a sheet attached to the wire.
Figure 6B:
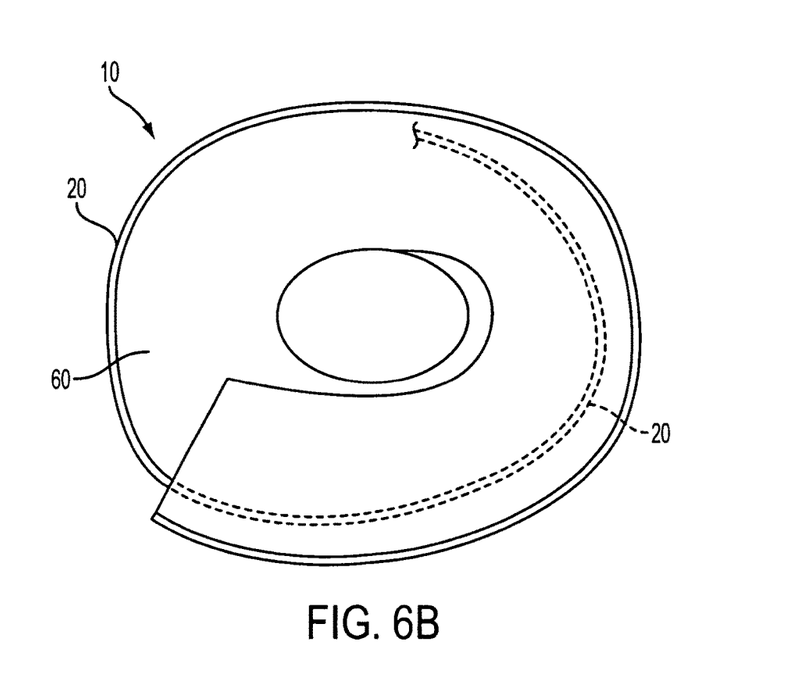
FIG. 6b is a bottom view showing a device with a sheet, according to an embodiment.

The device 10 may also include a sheet 60 that is attached to the wire 20. When the wire 20 is in its expanded linear shape, the sheet 60 may extend along the wire in a flagged manner such that the length of the sheet 60 extends in approximately the same direction as a longitudinal direction of the wire 20, as shown in the example of FIG. 6a. Also, when the wire 20 is in its expanded linear shape, the width of the sheet 60 extends in about a normal direction from the longitudinal direction of the wire 20. The length of the sheet 60 may be greater than the width of the sheet 60 when extended in this flagged manner. The length of the sheet 60 may extend along the wire 20 from the wire's proximal end 24 toward its distal end 22. For example, 50% or more of the proximal end of the wire 20 may be covered by the sheet 60. The length of the sheet 60 may extend along the entire length of wire 20. Alternatively, the length of the sheet 60 may extend along the proximal part of the wire for any length sufficient to ensure one or more of the most proximal orbits of the wire 20 are substantially or completely eclipsed by the sheet 60, as shown in the example of FIG. 6b, which shows a bottom view of the device 10. In another alternative, the length of the sheet 60 may extend along the proximal part of the wire for any length sufficient to ensure a proximal orbit of the wire 20 having a diameter at least equal to the opening of the left atrial appendage will be substantially or completely eclipsed by the sheet 60. In the example shown in FIG. 6b, the sheet substantially eclipses the bottom of the device 10. However, the device 10 may instead be arranged so that the sheet 60 completely eclipses the bottom of the device 10.

When the wire 20 is in its relaxed coil shape, the sheet 60 will cover one or more of the proximal orbits of the wire coil 20 such that an opening defined by a proximal orbit of the wire coil 20 or an interior cross-section of the wire coil 20 is substantially or completely eclipsed by the sheet 60 when the device 10 is viewed along the wire coil's 20 longitudinal axis. Alternatively, when the wire 20 is in its relaxed coil shape, the sheet 60 may cover proximal orbits of the wire 20 such that the interior cross-section of the coil shape is eclipsed by an overlapping of the sheet 60. The sheet 60 may be included on the proximal wire orbits 26 of the device 10 in order to effectively seal off the opening of the left atrial appendage. Sealing of the left atrial appendage with the sheet 60 effectively prevents blood flow into the left atrial appendage and/or any clots that may form in the left atrial appendage from migrating out of the left atrial appendage and into the bloodstream. Thus, the sheet 60 aids in the prevention of embolisms that would normally cause severe mental and physical disabilities or death.

The sheet 60 may be attached to the wire 20 by stitching around the wire. Other suitable means of attachment may be employed to ensure proper placement and fixation of the sheet 60 on the wire 20.

The sheet 60 may be made from a permeable or impermeable material for aiding the prevention of blood flow into the left atrial appendage and/or clot migration from the left atrial appendage. The sheet 60 may be made of fabric including polyester fibers such as Dacron®. Alternatively, the sheet may be made of another biocompatible material such as expanded polytetrafluoroethylene (ePTFE), Teflon®, felt, Gortex®, silicone urethane, metal fibers, or other polymers.

The sheet 60 may have an anti-coagulant coating or a coating to promote endothelial cell growth in order to aid in the prevention the clot formation around the sheet. The anti-coagulant coating may include heparin, an albumin-binding coating, phosphorylcholine, poly-D, L-lactic acid, prostaglandin, dextran sulfate, or other peptide suitable for coagulation prevention. The coating to promote endothelial cell growth may include pyrolytic carbon, a cryoprecipitate-based coating, autologous fibrin meshwork, elastin-based polypeptides, fibronectin, collagen IV, a fibronectin-collagen IV combination, extracellular matrix proteins and peptides, plasma polymerized coating, or other suitable material to encourage growth of endothelial cells on the sheet. The sheet coating is selected to further the purposes of the device by minimizing clot formation around the sheet in order to further reduce the risk of embolism when the device is used.

Figure 3:
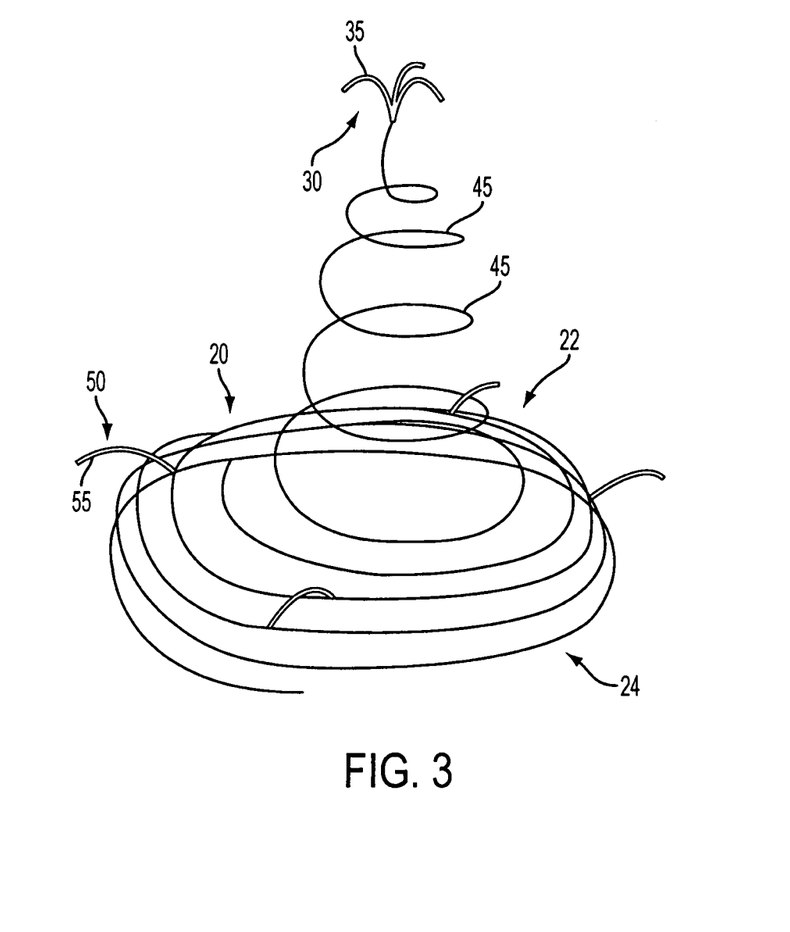
FIG. 3 is a side view of a second embodiment of a left atrial appendage occlusion device.

FIG. 3 shows a second embodiment of the device 10. The second embodiment is substantially the same as the first embodiment except the distal anchoring mechanism 30 has at least one anchor 35 attached directly to wire 20. In another aspect of the present invention, the wire 20 may include tension loops 45 that, when stretched, exert a force along the longitudinal direction of the wire 20, causing the proximal end 24 of wire 20 to be approximated against the opening of the left atrial appendage.

Figure 4:
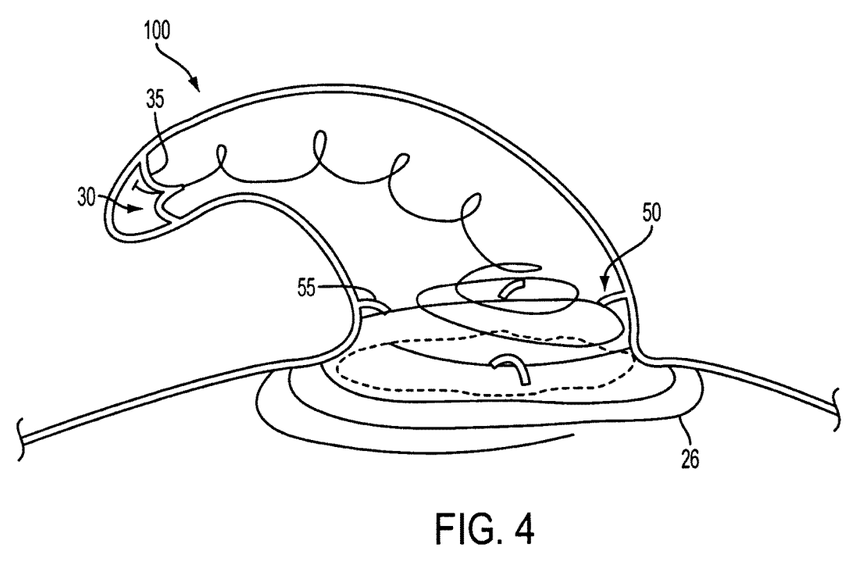
FIG. 4 is partial cross-sectional view of a left atrial appendage with a left atrial appendage occlusion device deployed therein.
Figure 5:
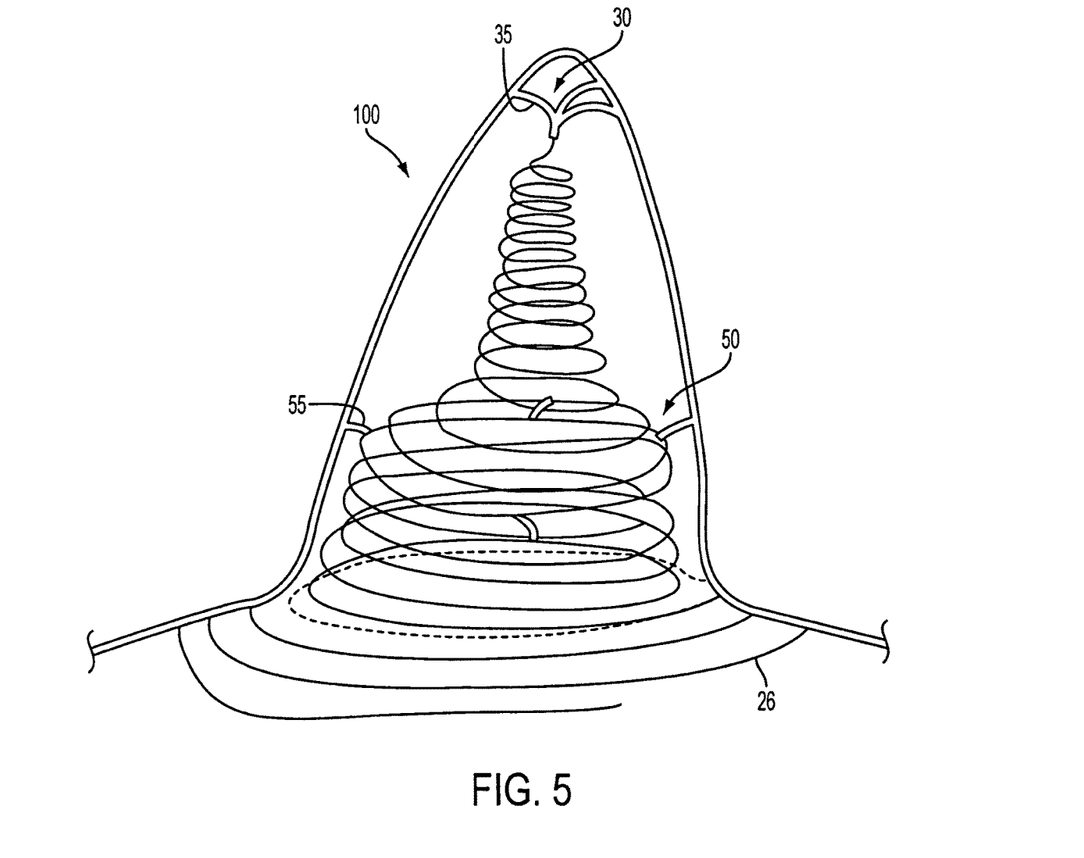
FIG. 5 is another partial cross-sectional view of a left atrial appendage with a left atrial-appendage occlusion device deployed therein.

FIGS. 4 and 5 shows the embodiment of FIG. 3 deployed into the left atrial appendage 100 of a heart. The present invention includes a method of closing the left atrial appendage 100 of a human or animal heart in order to aid in the prevention of blood flow into the left atrial appendage 100 and/or clot migration. The left atrial appendage occlusion device 10 is delivered to the left atrial appendage via a catheter. The device 10 is delivered in its expanded shape which is substantially linear. In its expanded state the distal anchoring mechanism 30, proximal anchoring mechanism 50, and sheet 60 fold against the wire.

The device is deployed such that the wire 20 is directed to form a substantially coiled shape in its relaxed state including a series of wire orbits or loops substantially within the left atrial appendage 100. Upon deployment, distal anchoring mechanism 30 is attached to distal end of the interior wall of the left atrial appendage 100 and the proximal anchoring mechanism 50 is attached to a more proximal portion of the interior wall of the left atrial appendage 100 to properly secure the device 10 in place. Alternatively, attachment may be achieved using only a distal anchoring mechanism 50. Anchoring of the device may be achieved by catching hook anchors 35 of the distal anchoring mechanism 30 to irregular trabeculations on the interior of the left atrial appendage 100. Similarly, hook anchors 55 of the proximal anchoring mechanism 50 may be attached to irregular trabeculations of the interior of the left atrial appendage. Alternatively, distal anchors 35 and proximal anchors 55 may be barbs attached to the wire coil 20. Attachment of the device would be accomplished by inserting the barbs into the wall of the left atrial appendage 100 and catching the barbs on the tissue. In another alternative attachment method, the anchors may be made of sutures and attachment is accomplished by suturing the distal anchoring mechanism 30 and proximal anchoring mechanism 50 to the interior wall of the left atrial appendage.

After deployment of the device 10, a number of proximal wire orbits of the coil may extend beyond the opening of the left atrial appendage and into the left atrium. Proximal orbits are sized such that their diameter will be larger than the diameter of the opening to the left atrial appendage 100 of substantially all patients to ensure proper sizing of the device, minimizing the need for measurement in each patient, and decreasing the time needed for proper implantation of the device. For example, a device 10 of a predetermined size and/or shape may be selected, based upon the results of a diagnostic test, such as angiography. Proximal orbits 26 of the wire coil 20 may be flush with the atrial wall and the sheet 60 will eclipse a proximal orbit 26 of the wire 20 to ensure the sheet 60 completely eclipses the opening of the left atrial appendage 100 in order to properly minimize migration of clots. Tension between the attached distal anchoring mechanism 30 and the proximal orbits 26 extending beyond the opening of the left atrial appendage 100 may hold the proximal orbits flush with the wall of the left atrium to ensure the sheet 60 completely eclipses the opening and is continuously flush with the left atrial wall to ensure complete prevention, or substantially complete prevention, of blood flow into the left atrial appendage 100 and/or clot migration into and out of the left atrial appendage 100.

Alternatively, proximal wire orbits 26 of the wire coil 20 may be within the opening of the left atrial appendage 100 and flush with a proximal portion of the wall of the left atrial appendage 100. The sheet 60 may eclipse a proximal wire orbit flush with the wall of the left atrial appendage 100 in order to prevent or substantially prevent blood flow into the left atrial appendage 100 and/or migration of blood clots into the left atrial appendage 100 or out of the left atrial appendage 100 and into the bloodstream.

Given the disclosure of the present invention, one versed in the art would appreciate that there may be other embodiments and modifications within the scope and spirit of the invention. Accordingly, all modifications attainable by one versed in the art from the present disclosure within the scope and spirit of the present invention are to be included as further embodiments of the present invention. The scope of the present invention is to be defined as set forth in the following claims.

What is claimed is:

1. A left atrial appendage occlusion device comprising:
   a deformable wire having a proximal portion and a distal portion, wherein the deformable wire is configured to form a first predetermined expanded shape and a second predetermined relaxed shape;
   a distal anchor that includes a plurality of hooks or barbs extending from a point at an overall distal end of the deformable wire, the distal anchor being configured to attach the device to an interior wall of the left atrial appendage; and
   a sheet attached to the proximal portion of the deformable wire,
   wherein the deformable wire and sheet are configured such that, when the deformable wire forms the first predetermined expanded shape:
   (i) the deformable wire has a substantially linear shape,
   (ii) a length of the sheet is substantially greater than a width of the sheet, the length of the sheet extending in about the same direction as a longitudinal direction of the deformable wire, and
   (iii) the width of the sheet extends in a flagged manner from the deformable wire in about a normal direction from the longitudinal direction of the deformable wire, and
   wherein the deformable wire and sheet are configured such that, when the deformable wire forms the second predetermined relaxed shape:
   (i) the deformable wire has a shape of a single substantially conical helix that includes a plurality of orbits that become progressively larger in a direction from the overall distal end of the deformable wire to an overall proximal end of the deformable wire, a distal-most orbit having a smallest diameter among the plurality of orbits and being adjacent to the distal anchor,
   (ii) a proximal orbit of the deformable wire has a diameter greater than a diameter of an opening of the left atrial appendage to be occluded, and
   (iii) the proximal orbit of the deformable wire is completely eclipsed by overlapping sections of the sheet.

2. The device of claim 1, wherein the deformable wire comprises a shape memory alloy comprising nickel titanium shape metal alloy.

3. The device of claim 1, wherein the distal anchor includes four of the hooks or barbs.

4. The device of claim 1, wherein the sheet extends proximate to the deformable wire over a length that is less than about ½ the deformable wire's length.

5. The device of claim 1, wherein the sheet is coated with a material to prevent coagulation.

6. The device of claim 5, wherein the material is a peptide.

7. The device of claim 1, wherein the sheet is coated with a material to promote endothelial cell growth.

8. The device of claim 1, wherein the sheet covers at least portions of the deformable wire forming two most proximal loops.

9. The device of claim 1, wherein the distal anchor is adapted to penetrate the interior wall of the left atrial appendage.

10. The device of claim 1, further comprising a proximal anchor attached to the proximal end of the deformable wire.

11. The device of claim 10, wherein the proximal anchor comprises hooks, barbs or sutures.

12. The device of claim 10, wherein the proximal anchor comprises four proximal anchors.

* * * * *